United States Patent [19]
Albrecht et al.

[11] 3,987,187
[45] Oct. 19, 1976

[54] FUNGICIDAL DISPERSIONS OF 2-METHYL-5,6-DIHYDROPYRAN-3-CARBOXYLIC ACID ANILIDE

[75] Inventors: Konrad Albrecht; Heinz Frensch, both of Frankfurt am Main; Kurt Hartel, Hofheim, Taunus, all of Germany

[73] Assignee: Hoechst Aktiengesellschaft, Frankfurt am Main, Germany

[22] Filed: Oct. 1, 1975

[21] Appl. No.: 618,572

Related U.S. Application Data

[63] Continuation of Ser. No. 432,826, Jan. 14, 1974, abandoned.

[30] Foreign Application Priority Data

Jan. 16, 1973   Germany............................ 2301922

[52] U.S. Cl................................. 424/283; 424/168
[51] Int. Cl.²........................................... A01N 9/28
[58] Field of Search............................ 424/283, 168

[56] References Cited
UNITED STATES PATENTS

3,632,821   1/1972   Scherer et al...................... 424/283

OTHER PUBLICATIONS

Doolittle, The Technology of Solvents & Plasticizers, p. 965.
Kiel et al., Chem. Abst., vol. 59, (1963), pp. 2970h–2971a.
Tsetlin et al., Chem. Abst., vol. 71, (1969), p. 122815f.
The Merch Index 8th Ed., (1968), pp. 31 & 32.

*Primary Examiner*—James O. Thomas, Jr.
*Assistant Examiner*—Allen J. Robinson
*Attorney, Agent, or Firm*—Curtis, Morris & Safford

[57]   ABSTRACT

Dispersions of 2-methyl-5,6-dihydropyran-3-carboxylic acid anilide in paraffinic mineral oils, liquid triglycerides and/or liquid esters of $C_1$ to $C_{12}$ monoalcohols have an improved effect against rust diseases and an extended spectrum of effectiveness against diseases caused by Colletotrichum types. The dispersions can be stabilized against crystal growth by adding aluminum chelates of certain hydroxy quinones, e.g. allzarin.

6 Claims, No Drawings

FUNGICIDAL DISPERSIONS OF 2-METHYL-5,6-DIHYDROPYRAN-3-CARBOXYLIC ACID ANILIDE

This is a continuation of application Ser. No. 432,826, filed Jan. 14, 1974, and now abandoned.

The present invention relates to fungicidal dispersions of 2-methyl-5,6-dihydropyran-3-carboxylic acid anilide.

2-Methyl-5,6-dihydropyran-3-carboxylic acid anilide is known from Belgian Pat. No. 727,245 as a fungicidal agent for combatting rust diseases, for example Rhizoctonia and smut diseases. The spectrum of effectiveness is, however, rather limited. To combat diseases localized in the foliage or fruits, for example Colletotrichum lindemuthianum in beans and Colletotrichum coffeanum in coffee berries this compound has been unsuitable so far.

It has now been found that by dispersing the active compound in paraffinic mineral oils, liquid triglycerides and/or liquid esters of higher alcohols its effect against rust diseases is greatly improved, and moreover its spectrum of effectiveness is extended to diseases caused by Colletotrichum types, such as Anthracnose of beans (Colletotrichum lindemuthianum) and coffee berry disease (Colletotrichum coffeanum).

The present invention provides fungicidal dispersions of 2-methyl-5,6-dihydropyran-3-carboxylic acid anilide containing paraffinic mineral oils, liquid triglycerides and/or liquid esters of $C_1$ to $C_{12}$ monoalcohols, optionally in combination with further usual formulation auxiliaries.

Suitable dispersion media for the dispersions of the invention are, for example, 1. straight chain or branched $C_8$ to $C_{25}$ paraffins having boiling points above 140° C, preferably above 260° C, for example nonane, decane, undecane, dodecane, tridecane, tetradecane, pentadecane, hexadecane, or mixtures thereof with higher boiling homologs, such as hepta-, octa-, nonadecane, eicosane, heneicosane, docosane, tricosane, tetracosane, pentacosane, and the branched chain isomers thereof;

2. liquid triglycerides, for example vegetable oils such as rape-seed oil, arachis oil, sunflower oil, cotton seed oil;

3. liquid esters of $C_1$ to $C_{12}$ monalcohols with $C_2$ to $C_{10}$ carboxylic acids, such esters containing at least 8 and in the case of esters of monobasic acids at most 12 carbon atoms and in the case of esters of dibasic acids at most 32 carbon atoms. Suitable esters are, for example, those of aliphatic $C_6$ to $C_{10}$ carboxylic acids, for example caproic acid, capric acid, caprylic acid and pelargonic acid; or of aromatic carboxylic acids such as benzoic acid, toluylic acid, salicylic acid and phthalic acid. Suitable alcohol components in these esters are, for example butanol, n-octanol, i-octanol, dodecanol, cyclopentanol, cyclohexanol, cyclooctanol, or benzyl alcohol. Esters to be used in the dispersions of the invention are thus, for example, benzyl acetate, caproic acid ethyl ester, pelargonic acid ethyl ester, benzoic acid methyl or ethyl ester, salicylic acid methyl, propyl, or butyl ester, preferably, however, diesters of phthalic acid with saturated aliphatic or alicyclic $C_1$ to $C_{12}$ alcohols, such as phthalic acid dimethyl ester, dibutyl ester, diisooctyl ester, didodecyl ester, dicyclopentyl ester, dicyclohexyl ester, or dicyclooctyl ester.

The dispersions of the invention are prepared by known methods by grinding the active compound dispersed in the dispersion medium in a colloid mill, ball mill, sand mill, and preferably in grinding ball mills, optionally with the addition of further usual formulation auxiliaries such as emulsifiers, dispersion media, wetting agents or adhesives.

The content of active ingredient of the dispersions is in the range of from 5 to 50 % by weight, preferably 15 to 30 % by weight. Highly concentrated dispersions containing 50 % by weight of active ingredient or slightly less are used as ultra low volume (ULV) preconcentrates. They may contain further additions of formulation auxiliaries but are unsuitable for direct application owing to their high viscosity; rather they are diluted prior to application. Suitable diluents for this purpose are, in the first place, the mineral oil, triglyceride or ester used for preparing the dispersion to which emulsifiers, wetting agents, adhesives, or dispersion media may be added according to the requirements in each case. It is also possible, of course, to use mixtures of mineral oils, triglycerides and/or esters for making dispersions ready for application. In general, the proportion of emulsifiers and dispersion media in the total dispersion is below 20 %, wetting agents and adhesives can be added to the dispersion in an amount of up to 5%.

Suitable emulsifiers and dispersion media are substituted alkylphenol polyglycol ethers, such as octyl-, nonyl-, or triisobutylphenol polyglycol ether, natural fatty alcohol polyglycol ethers as well as polyglycol ethers of synthetic alcohols, preferably isotridecanol polyglycol ether, fatty acid polyglycol esters, and mixtures of ethoxylated substances, optionally in combination with calcium salts of alkyl-benzene or paraffin--sulfonic acids and chlorinated paraffin-sulfonic acids.

Suitable wetting agents are, for example, emulsifiers such as oxethylated alkylphenols, salts of alkyl- or arylsulfonic acids or salts of oleylmethyl tauride.

The dispersions in accordance with the invention are readily pourable in the preferred range of from 15 to 30 % of active ingredient, their viscosity in the range of application is below 5, preferably below 3 poises, depending on the content of active ingredient, and they can be dispersed both in water or paraffin oils in any desired proportion. Depending on the degree of dilution, they can be applied according to the low volume or ultra low volume process by aeroplanes or with soil application devices.

Owing to the fact that crystals of 2-methyl-5,6-dihydropyran-3-carboxylic acid anilide have a pronounced tendency to grow when in the form of a dispersion (a sample in which the active compound was ground to a particle size of less than 10 microns contained crystals of a length of over 100 microns after a four week storage at 50° C) a stabilizer should preferably be added to the dispersions to obtain the required stability in storage, especially if the formulation is destined for use in tropical countries or for prolonged shipment. Surprisingly, an excellent stability in storage can be obtained by adding to the dispersions aluminum chelate compounds of aromatic polynuclear quinones containing hydroxy groups in alpha and preferably in peri-position to an oxygen atom of the quinone grouping, such as naphthazarin, quinizarin, crysazin, and preferably alizarin. Chelates of this type generally contain the atom grouping

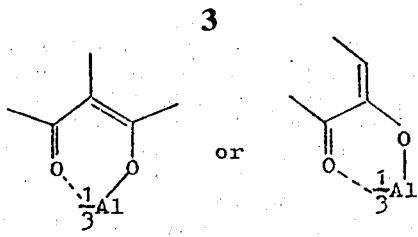

The preparation of aluminum chelates is described in Chemische Berichte 46, pages 451 et seq. The addition of chelates of this type strongly reduces crystal growth. In a test of long duration at 50° C the particles still had a particle size below 10 microns on the average even after a 2 month storage. A storage under these conditions generally corresponds to a storage for 2 years at normal temperature.

The amounts of aluminum chelate necessary for stabilizing the oil dispersions of the invention are, in general, in the range of from about 0.2 to about 5 % by weight, preferably 0.4 to 1 % by weight, calculated on the total formulation. Amounts higher than 5 % may also be added, but offer no additional advantage.

Aluminum chelate compounds can be added to the dispersion either per se or in the form of their starting components (aluminum salts or aluminum hydroxide, preferably aluminum acetate, and an aromatic quinone, preferably alizarin) prior to its preparation. In the latter case the chelate compounds are formed during the grinding of the formulation components, which in the case of alizarin can be perceived by the change in color from yellow orange to red. When the starting components are used aluminum compound and quinone are added in stoichiometric amounts or, for the sake of simplicity, in equal amounts by weight.

The stabilized oil dispersions of 2-methyl-5,6-dihydropyran-3-carboxylic acid anilide have the same biological effect than the unstabilized freshly prepared disperions; they are especially characterized by the aforesaid extended range of activity against Colletotrichum species. Owing to their long stability in storage at +50° C they comply with international standards and ensure a reliable application and safe combating result.

The following examples illustrate the invention, in the biological examples the infestation of untreated plants being equal to 100.

EXAMPLES OF PREPARATION

EXAMPLE 1

In a grinding ball mill operated with quartz beads having a diameter of 1 to 2 mm the following mixture was ground until the particles had a size of less than 5 microns:
15 % by weight of 2-methyl-5,6-dihydropyran-3 carboxylic acid anilide
8 % by weight of alkyl-phenol polyglycol ether (Triton X 207)
4 % by weight of isotridecanol polyglycol ether (Genapol X-080) and
73 % by weight of paraffinic mineral oil (Essobayol 90 of Esso AG.) (An industrial grade of white oil).

The ground mixture had a viscosity of 3 poises at room temperature and was well dispersible in water. It could also be diluted easily with other paraffinic oils. When stored at 50° C, the product contained after 4 weeks interlaced crystal needles of a length of 120 to 180 microns. The solid matter was poorly dispersible in water and flocculated rapidly. The biological effect was strongly reduced.

EXAMPLE 2

The following mixture was ground in the mill of Example 1:
15 % by weight of 2-methyl-5,6-dihydropyran-3-carboxylic acid anilide
8 % by weight of alkyl-phenol polyglycol ether (Triton X-207)
4 % by weight of isotridecanol polyglycol ether (Genapol X-080)
1 % by weight of aluminum chelate of alizarin and
72 % by weight of paraffinic mineral oil (Essobayol 90 of Esso AG).

The dispersion was readily pourable, it had a viscosity of 2.5 poises and could be well dispersed in water and paraffinic oils. It had the same properties as the dispersion of Example 1 and complied with all application requirements. After a 2 month storage at 50° C, only a few crystals having a length above 12 microns could be detected. The majority of the crystals were less than 10 microns long. The dispersion was stable and could be used in the same manner as prior to storage. Within the limits of error the biological activity of the stored product was equal to that of the freshly prepared product.

EXAMPLE 3

In the manner described in Examples 1 and 2 the following mixture was ground:
15 % by weight of 2-methyl-5,6-dihydropyran-3-carboxylic acid anilide
8 % by weight of alkyl-phenol polyglycol ether (Triton X-207)
4 % by weight of isotridecanol polyglycol ether (Genapol X-080)
0.5 % by weight of alizarin
0.5 % by weight of aluminum acetate and
72 % by weight of paraffinic mineral oil (Essobayol 90)

During the course of grinding the originally orange yellow color of the dispersion turned red. The dispersion had the same properties and the same stability in storage as the dispersion of Example 2.

EXAMPLE 4

In the manner described in Examples 1 to 3 the following mixture was ground:
25 % by weight of 2-methyl-5,6-dihydropyran-3-carboxylic acid anilide
8 % by weight of alkyl-phenol polyglycol ether (Triton X-207)
4 % by weight of isotridecanol polyglycol ether (Genapol X-080)
62 % by weight of paraffinic mineral oil (Essobayol 90) and
1 % by weight of aluminum chelate of alizarin.

This dispersion had the same properties as the dispersions of Examples 3 and 2, its viscosity being 4.5 poises. The crystal growth of the active compound could be substantially avoided in this case, too. After a 2 month storage at 50° C, the maximum crystal size was 12 microns.

EXAMPLE 5

In the manner described in Examples 1 to 3 the following mixture was ground:

20 % by weight of 2-methyl-5,6-dihydropyran-3-carboxylic acid anilide
10% by weight of isotridecanol polyglycol ether (Genapol X-080)
69% by weight of phthalic acid isooctyl ester and
0.5 % by weight of aluminum chelate of alizarin.

Due to the presence of the aluminum complex this dispersion was likewise stable in storage in contrast to an analogous formulation prepared without the dyestuff. The dispersion was pourable, dispersible in water and oil and had a good biological effect. When the formulations of Examples 2 to 5 were prepared without alizarin-chelate component, crystal growth occurred during storage as in the dispersion of Example 1.

EXAMPLE 6

In the manner described in Examples 1 to 3, the following mixture was ground:
35 % by weight of 2-methyl-5,6-dihydropyran-3-carboxylic acid anilide
10 % by weight of alkyl-phenol polyglycol ether (Triton X-207)
5 % by weight of isotridecanol polyglycol ether (Genapol X-080)
46 % by weight of paraffinic mineral oil (Shellsol K) (an industrial grade white oil)
2 % by weight of chrysazin
2 % by weight of basic aluminum acetate After a 2 month storage at 50° C, the formulation contained only a few crystals having a length of 15 microns at the most.

EXAMPLE 7 (Wettable powder)(comparative example)

A mixture of
50 % by weight of 2-methyl-5,6-dihydropyran-3-carboxylic acid anilide
15 % by weight of magnesium carbonate
15 % by wieght of sodium bicarbonate
5 % by weight of sodium dinaphthylmethane-disulfonate
2 % by weight of polyvinyl alcohol
1 % by weight of sodium dibutylnaphthalene-sulfonate and
12 % by weight of milk powder (skimmed)
was ground twice in a disk attrition mill at the highest speed of rotation. The powder obtained was excellently suspendible.

BIOLOGICAL EXAMPLES

EXAMPLE I

The dispersions of Examples 1 to 5 were used in a greenhouse test to combat Anthracnose of beans (Colletotrichum lindemuthianum). For this purpose, kidney bean plants were cultivated, the plants were infested in the early stage of primary leaves with conidia of Colletotrichum lindemuthianum causing the disease, and placed drip wet for 24 hours in a chamber having a relative humidity of 100 % and a temperature of 18° c. Subsequently, the plants were transferred to the greenhouse having a relative humidity of 85 - 90 % and 3 days after infestation they were sprayed to the drip off with the formulations of Examples 1 to 5 in aqueous suspension in an amount of 500, 250, and 125 mg. of active compound per liter of spray liquor. For comparison, infested plants were sprayed drip wet with a wettable powder formulation containing 50 % of active compound according to Example 7 in the same concentrations of active compound. After drying of the coating containing the active ingredient, the plants were placed again into the greenhouse and examined as to the degree of infestation with Anthracnose of beans 21 days after infestation. The results of the following Table I show that the formulations according to the invention had a very good effect against Anthracnose of beans, whereas the wettable powder formulation was practically ineffective.

TABLE I

| formulation according to Example | % infestation with Colletotr. in beans with mg of active compound/l of spray liquor | | |
|---|---|---|---|
| | 500 | 250 | 125 |
| 1 (freshly prepared) | 0 | 0 | 18 |
| 2 (freshly prepared) | 0 | 0 | 12 |
| 2 (stored for 3 months at 50° C) | 0 | 0 | 13 |
| 3 (freshly prepared) | 0 | 0 | 10 |
| 4 (freshly prepared) | 0 | 0 | 10 |
| 5 (freshly prepared) | 0 | 0 | 12 |
| 7 (wettable powder) | 43 | 63 | 80 |
| untreated infested plants | 100 | | |

EXAMPLE II

The dispersions according to Examples 1 to 5 were used for the curative treatment of rust infested wheat. For this purpose, wheat plants in the three leaf stage were strongly infested with brown rust and placed drip wet for 24 hours in a chamber at a temperature of 20° C and 100 % of relative humidity. Subsequently, the plants were transferred into the greenhouse at 20° C and 5 days after infestation, the plants were sprayed to the drip off with the formulations of Examples 1 to 5 in a concentration of 500, 250, 125 and 60 mg of active compound per liter of spray liquor. As comparative agent the wettable powder according to Example 7 was used in the same concentrations. After a time of incubation of 14 days, the plants were examined as to the degree of infestation with brown rust. The results are listed in Table II in comparison to untreated infested plants.

TABLE II

| formulation according to Example | % infestation with brown rust of wheat mg/active compound/ liter of spray liquor | | | |
|---|---|---|---|---|
| | 500 | 250 | 125 | 60 |
| 1 (freshly prepared) | 0 | 0 | 0 | 15 |
| 2 (freshly prepared) | 0 | 0 | 0 | 8 |
| 2 (stored for 3 months at 50° C) | 0 | 0 | 0 | 10 |
| 3 (freshly prepared) | 0 | 0 | 0 | 10 |
| 4 (freshly prepared) | 0 | 0 | 0 | 10 |
| 5 (freshly prepared) | 0 | 0 | 0 | 8 |
| 7 (wettable powder) | 0 | 0 | 18 | 30 |

TABLE II-continued

| formulation according to Example | % infestation with brown rust of wheat mg/active compound/ liter of spray liquor | | | |
|---|---|---|---|---|
| | 500 | 250 | 125 | 60 |
| untreated and infested plants | | 100 | | |

EXAMPLE III

The dispersions of Examples 1 to 5 were used for the following test:

After having reached a height of 15 cm, young coffee plants were strongly infested with spores of coffee rust (Hemileia vastatrix) and placed drip wet for 3 days in a chamber at 22° C and 100 % of relative humidity. Subsequently, the plants were transferred into the greenhouse having a temperature of 22°–23° C and a relative humidity of 85–95% and 5 days after they were sprayed to the drip off with the formulations of Examples 1 to 5 in a concentration of 500, 250, 125 and 60 mg of active compound per liter of spray liquor. For comparison, the wettable powder formulation of Example 7 was used in the same concentrations of active compound.

After drying of the coating containing the active ingredient, for each concentration 50 pieces of about 3 × 3 cm were cut from the leaves and with their upper side the cuttings were placed in groups of 10 pieces each on moist filter paper in glass dishes. Conidia of coffee rust were dropped again onto the cuttings and the covered 5 glass dishes for each concentration were placed in the greenhouse at 22° C.

After an incubation time of 4 weeks, the pieces of leaves were examined as to their infestation with coffee rust. The result is listed in Table III in comparison to untreated infested leaf pieces. It can be seen that the formulations in accordance to the invention had a much better effect against coffee rust than the conventional wettable powder formulation.

TABLE III

| formulation according to Example | % infestation with coffee rust /mg of active compound/liter of spray liquor | | | |
|---|---|---|---|---|
| | 500 | 250 | 125 | 60 |
| 1 (freshly prepared) | 0 | 0 | 0 | 18 |
| 2 (freshly prepared) | 0 | 0 | 0 | 10 |
| 2 (stored for 3 months at 50° C) | 0 | 0 | 0 | 12 |
| 3 (freshly prepared) | 0 | 0 | 0 | 12 |
| 4 (freshly prepared) | 0 | 0 | 0 | 12 |
| 5 (freshly prepared) | 0 | 0 | 0 | 10 |
| 7 (wettable powder) | 0 | 10 | 28 | 42 |
| untreated infested leaves | | 100 | | |

EXAMPLE IV

Field test with unstabilized oil dispersion:

In a coffee plantation in Kenia which showed regularly a strong infestation with coffee rust (Hemilia vastatrix) and also a strong infestation with coffee berry disease (CBD) caused by the fungus Colletotrichum coffeanum, 4 coffee trees each were sprayed to the drip off with an aqueous suspension of an oil dispersion formulation according to Example 4, which did not contain, however, the aluminum alizarin stabilizer. The applied concentrations of active ingredient were 500 and 250 mg per liter of spray liquor.

For comparison, aqueous suspensions of the wettable powder formulation according to Example 7 were used in concentrations of 1,000 and 500 mg of active compound per liter of spray liquor. The spray liquors were applied with a Holder knapsack sprayer.

Four groups of trees each were treated 6 times during the main infestation period from February through July and the trees were examined as to their degree of infestation in the middle of August, i.e. 3 weeks after the last treatment. The average values of the 4 groups are summarized in the following Table IV, the degree of infestation of untreated trees being 100.

TABLE IV

| formulation | infested with | mg of active compound per liter of spray liquor | | |
|---|---|---|---|---|
| | | 1,000 | 500 | 250 |
| | coffee rust (% of infested leaf surface) | | | |
| oil dispersion | | | 8 | 18 |
| wettable powder | | 32 | 58 | |
| untreated | | | 100 | |
| | coffee berry disease (% of infested berries) | | | |
| oil dispersion | | | 15 | 39 |
| wettable powder | | 70 | 88 | |
| untreated | | | 100 | |

What is claimed is:

1. A fungicidal dispersion comprising 5 to 50% by weight of 2-methyl-5,6-dihydropyran-3-carboxylic acid anilide, said anilide being dispersed in at least one of the following dispersants: $C_a$ to $C_{2K}$ paraffins boiling at a temperature above 140° C, rape-seed oil, arachis oil, sunflower oil, cotton seed oil, a liquid monoester formed of monoalcohols of 1 to 12 carbon atoms with $C_2$ to $C_{10}$ monobasic carboxylic acids, wherein the ester has at least 8 carbon atoms and up to 12 carbon atoms, a liquid ester of monoalcohols of 1 to 12 carbon atoms and a dibasic acid of $C_2$ to $C_{10}$ carbon atoms wherein said ester has at least 8 and up to 32 carbon atoms, or mixtures of said esters, and, as stabilizer for said anilide, 0.2 to 5% by weight of an aluminum chelate of a polynuclear hydroxy-quinone selected from the group consisting of napththazarin, quinizarin, chrysazim, and alizarin.

2. The fungicidal dispersion as claimed in claim 1, wherein the liquid ester is a diester of phthalic acid.

3. The fungicidal dispersion as claimed in claim 1, wherein the diester is phthalic acid diisooctyl ester.

4. The fungicidal dispersion as claimed in claim 1, wherein the content of active compound is in the range of from 15 to 30% by weight.

5. The fungicidal dispersion as claimed in claim 1, containing up to 20% by weight of an emulsifier, and up to 5% by weight of a wetting agent, an adhesive or mixtures thereof, the percentages being calculated on said dispersion by weight.

6. The fungicidal dispersion as claimed in claim 1, wherein the chelate content is in the range of from 0.4 to 1% by weight based on the total dispersion by weight.

* * * * *